United States Patent
Akui

(10) Patent No.: US 8,926,500 B2
(45) Date of Patent: Jan. 6, 2015

(54) LIGHT IRRADIATING DEVICE, SCANNING ENDOSCOPIC DEVICE, MANUFACTURING METHOD OF LIGHT IRRADIATING DEVICE, AND MANUFACTURING METHOD OF SCANNING ENDOSCOPIC DEVICE

(71) Applicant: Olympus Medical Systems Corp., Tokyo (JP)

(72) Inventor: Nobuaki Akui, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/929,086

(22) Filed: Jun. 27, 2013

(65) Prior Publication Data

US 2013/0345508 A1    Dec. 26, 2013

Related U.S. Application Data

(63) Continuation of application No. PCT/JP2012/078720, filed on Nov. 6, 2012.

(30) Foreign Application Priority Data

Jan. 11, 2012    (JP) .................................. 2012-003478

(51) Int. Cl.
*A61B 1/04* (2006.01)
*A61B 1/07* (2006.01)
*A61B 1/06* (2006.01)
*A61B 1/00* (2006.01)

(52) U.S. Cl.
CPC ............... *A61B 1/0638* (2013.01); *A61B 1/04* (2013.01); *A61B 1/00045* (2013.01); *A61B 1/00114* (2013.01); *A61B 1/0011* (2013.01); *A61B 1/0002* (2013.01); *A61B 1/0669* (2013.01); *A61B 1/00172* (2013.01); *A61B 1/00009* (2013.01); *A61B 1/07* (2013.01); *A61B 1/00186* (2013.01)
USPC .......................................... 600/109; 600/177

(58) Field of Classification Search
USPC ................. 600/104, 109, 127–130, 160, 172, 600/175–177; 348/45, 65, 68; 362/574; 385/117–119; 396/17
See application file for complete search history.

(56) References Cited

FOREIGN PATENT DOCUMENTS

| JP | A-10-014858 | 1/1998 |
|----|-------------|--------|
| JP | A-2003-315612 | 11/2003 |

(Continued)

OTHER PUBLICATIONS

International Search Report issued in Application No. PCT/JP2012/078720; Dated Jan. 8, 2013 (With Translation).

(Continued)

*Primary Examiner* — Alireza Nia
*Assistant Examiner* — Timothy J Neal
(74) *Attorney, Agent, or Firm* — Oliff PLC

(57) ABSTRACT

In a light irradiating device of a scanning endoscopic device, a proximal end of a lens optical system is located apart from a distal end of an optical fiber in directions parallel to the longitudinal axis, and a lens-side facing portion faces a fiber-side facing portion apart from the fiber-side facing portion by a second dimension smaller than a first dimension between the distal end of the optical fiber and the proximal end of the lens optical system in the directions parallel to the longitudinal axis. The proximal end of the lens optical system and the distal end of the optical fiber are located between a distal end and a proximal end of the window in the directions parallel to the longitudinal axis.

18 Claims, 8 Drawing Sheets

(56) References Cited

FOREIGN PATENT DOCUMENTS

| JP | A-2004-024888 | 1/2004 |
|----|---------------|--------|
| JP | A-2010-088665 | 4/2010 |
| JP | A-2010-284261 | 12/2010 |
| JP | A-2011-036460 | 2/2011 |
| JP | A-2011-104239 | 6/2011 |
| WO | WO 2005/121862 | 12/2005 |

OTHER PUBLICATIONS

Jul. 24, 2014 International Preliminary Report on Patentability issued in International Patent Application No. PCT/JP2012/078720 (English translation only).

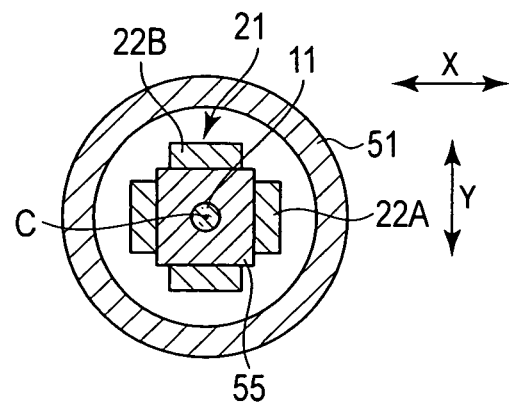
F I G. 5
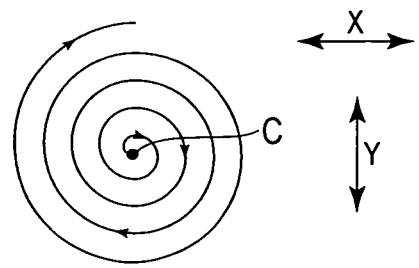
F I G. 6

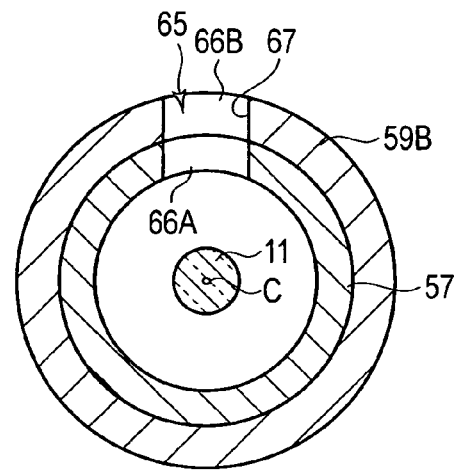
F I G. 9
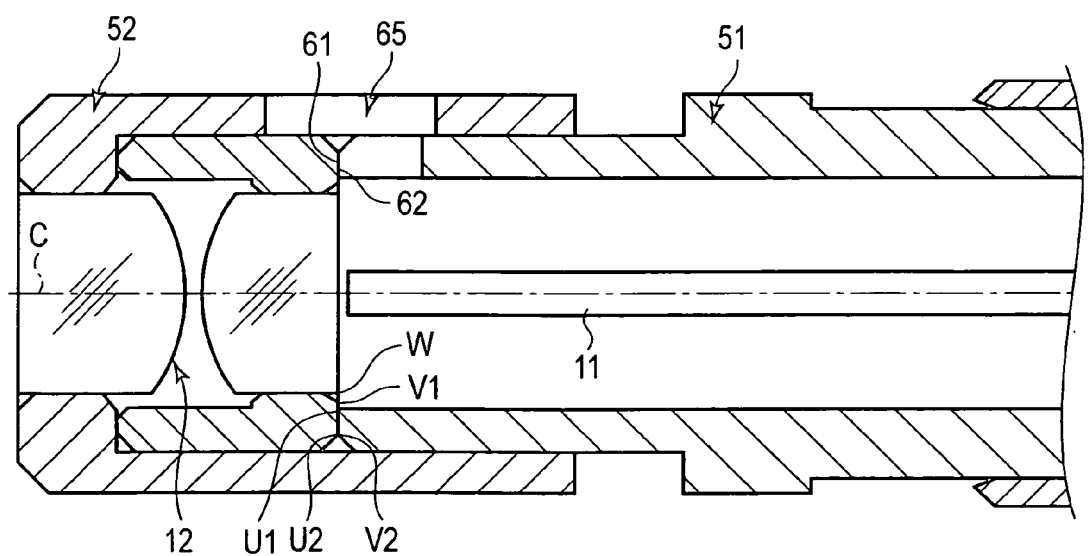
F I G. 10

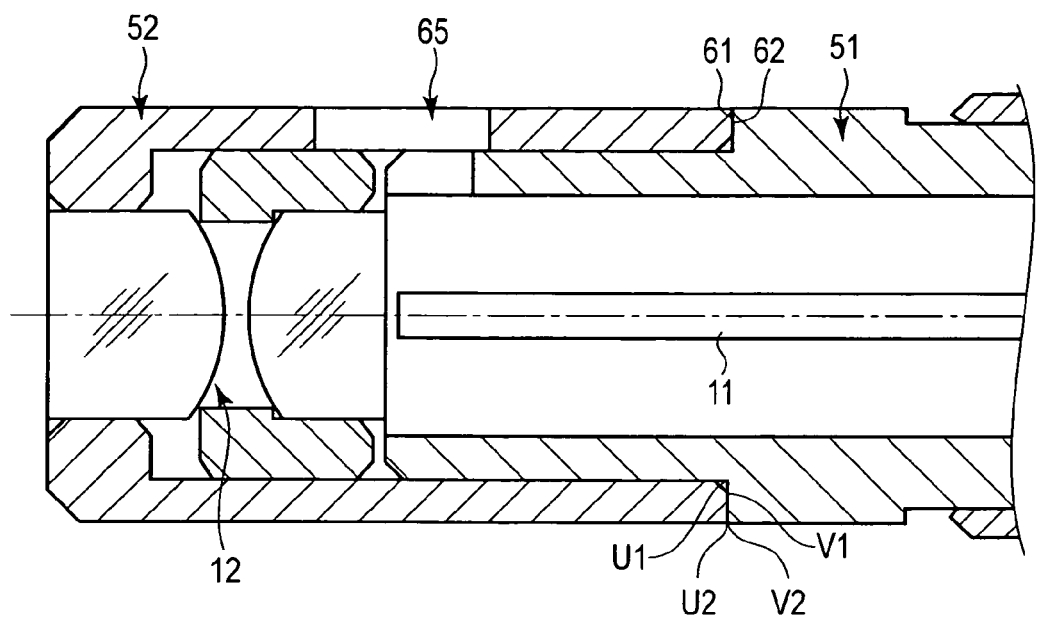
F I G. 13

LIGHT IRRADIATING DEVICE, SCANNING ENDOSCOPIC DEVICE, MANUFACTURING METHOD OF LIGHT IRRADIATING DEVICE, AND MANUFACTURING METHOD OF SCANNING ENDOSCOPIC DEVICE

CROSS-REFERENCE TO RELATED APPLICATIONS

This is a Continuation Application of PCT Application No. PCT/JP2012/078720, filed Nov. 6, 2012 and based upon and claiming the benefit of priority from prior Japanese Patent Application No. 2012-003478, filed Jan. 11, 2012, the entire contents of which are incorporated herein by reference.

BACKGROUND OF THE INVENTION

1. Field of the Invention

The present invention relates to a scanning endoscopic device which is configured to scan a subject to generate an image of the subject, and a light irradiating device which is used in the scanning endoscopic device and which is configured to irradiate (apply) light to the subject. The present invention also relates to a manufacturing method of the light irradiating device, and a manufacturing method of the scanning endoscope of the scanning endoscopic device.

2. Description of the Related Art

Jpn. Pat. Appln. KOKAI Publication No. 2011-36460 has disclosed a medical observation system including a light irradiating device which is configured to irradiate (apply) light from a light source to a subject. In the light irradiating device of this medical observation system, light guided from the light source is emitted from the distal end of an optical fiber (light fiber), and the emitted light is collected to a subject by a lens optical system. The light irradiating device includes a piezoelectric actuator which is an actuator section configured to drive the optical fiber. In the piezoelectric actuator, ultrasonic vibrations are generated by a supply of a drive current. In response to the transmission of the vibrations to the optical fiber, the distal end of the optical fiber moves on a substantially planar surface perpendicular to a longitudinal axis, and the position of the distal end of the optical fiber changes with time. As the position of the emission of the light from the optical fiber changes with time, a position in the subject where the light is collected by the lens optical system changes with time. The medical observation system also includes a light guide which is configured to receive, with time, light reflected from the collection position in the subject. The received light is guided to a light detector (photodetector) by the light guide. The kind and intensity of light are detected by the light detector with time. In this way, the subject is scanned in the medical observation system. In the light detector, an electrical signal based on the detected kind and intensity of light is generated. The light collection position in the subject is detected with time. An image of the subject is generated in an image processing section such as an image processing circuit based on the electrical signal generated in the light detector and the detected collection position.

Jpn. Pat. Appln. KOKAI Publication No. 2010-284261 has disclosed a light irradiating device used in a scanning endoscope, for example. In this light irradiating device, light is irradiated to a subject as in the light irradiating device according to Jpn. Pat. Appln. KOKAI Publication No. 2011-36460. When this light irradiating device is manufactured, a fiber-side cylindrical portion to which an optical fiber is attached is moved along a longitudinal axis relative to a lens-side cylindrical portion to which a lens optical system is fixed, and a dimension between the distal end of the optical fiber and the proximal end of the lens optical system is adjusted. The dimension between the distal end of the fiber and the proximal end of the lens optical system is then adjusted so that the light is collected to the subject by the lens optical system. Thus, the fiber-side cylindrical portion is fixed to the lens-side cylindrical portion.

Jpn. Pat. Appln. KOKAI Publication No. 2003-315612 has disclosed a light collimator which uses a lens optical system to collimate light emitted from the distal end of the optical fiber. When this light collimator is manufactured, a fiber-side cylindrical portion to which an optical fiber is attached is moved along a longitudinal axis relative to a lens-side cylindrical portion to which a lens optical system is fixed, and a dimension between the distal end of the optical fiber and the proximal end of the lens optical system is adjusted. Here, a through-hole is provided in the lens-side cylindrical portion along diametrical directions from an outer portion to an inner portion. During manufacture, the relative positions of the lens optical system (lens-side cylindrical portion) and the fiber-side cylindrical portion are adjusted through the through-hole. After the lens optical system and the fiber-side cylindrical portion are adjusted to proper relative positions, the fiber-side cylindrical portion is fixed to the lens-side cylindrical portion.

BRIEF SUMMARY OF THE INVENTION

According to one aspect of the invention, a light irradiating device in a scanning endoscopic device which is configured to scan a subject to generate an image of the subject, the light irradiating device including: an optical fiber which is extended along an longitudinal axis, and which is configured to emit, from a distal end thereof, light guided from a proximal direction to a distal direction; a lens optical system which is disposed so that a proximal end thereof is located apart from the distal end of the optical fiber in directions parallel to the longitudinal axis, and which is configured to collect the light emitted from the optical fiber to the subject; a cylindrical unit, the cylindrical unit including a fiber-side cylindrical portion to which the optical fiber is attached so that the movement of the optical fiber along the longitudinal axis is regulated, and a lens-side cylindrical portion to which the lens optical system is fixed and which is provided coaxially with the fiber-side cylindrical portion; a fiber-side facing portion which is provided in the fiber-side cylindrical portion so that the fiber-side facing portion faces in the distal direction; a lens-side facing portion which is provided in the lens-side cylindrical portion so that the lens-side facing portion faces in the proximal direction, and which faces the fiber-side facing portion apart from the fiber-side facing portion by a second dimension smaller than a first dimension between the distal end of the optical fiber and the proximal end of the lens optical system in the directions parallel to the longitudinal axis; and a window defining portion which defines a window provided along diametrical directions from an outer portion to an inner portion of the cylindrical unit, the window defining portion defining the window so that the proximal end of the lens optical system and the distal end of the optical fiber are located between a distal end and a proximal end of the window in the directions parallel to the longitudinal axis.

According to one another aspect of the invention, a manufacturing method of a light irradiating device of a scanning endoscopic device which is configured to scan a subject to generate an image of the subject, the manufacturing method including: attaching an optical fiber to a fiber-side cylindrical portion of a cylindrical unit so that the movement of the optical fiber along a longitudinal axis is regulated, the optical fiber being extended along the longitudinal axis, and being configured to emit, from a distal end thereof, light guided from a proximal direction to a distal direction; fixing a lens optical system to a lens-side cylindrical portion of the cylindrical unit, the lens optical system having a proximal end thereof located apart from the distal end of the optical fiber in directions parallel to the longitudinal axis in an in-focus condition, the lens optical system being configured to collect the light emitted from the optical fiber to the subject in the in-focus condition; forming, in the fiber-side cylindrical portion, a fiber-side facing portion which faces in the distal direction in the in-focus condition; forming a lens-side facing portion in the lens-side cylindrical portion, the lens-side facing portion facing in the proximal direction in the in-focus condition, the lens-side facing portion facing the fiber-side facing portion apart from the fiber-side facing portion by a second dimension smaller than a first dimension between the distal end of the optical fiber and the proximal end of the lens optical system in the directions parallel to the longitudinal axis in the in-focus condition; forming a hole which forms a window in the in-focus condition along diametrical directions from an outer portion to an inner portion of the cylindrical unit, the hole being formed so that the proximal end of the lens optical system and the distal end of the optical fiber are located between a distal end and a proximal end of the window in the directions parallel to the longitudinal axis in the in-focus condition; adjusting relative positions of the fiber-side cylindrical portion and the lens-side cylindrical portion in the directions parallel to the longitudinal axis to positions in the in-focus condition through the window formed in the cylindrical unit so that the lens optical system fixed to the lens-side cylindrical portion is located to the distal direction side of the optical fiber attached to the fiber-side cylindrical portion and so that the fiber-side cylindrical portion and the lens-side cylindrical portion are disposed coaxially with the longitudinal axis; and fixing the fiber-side cylindrical portion and the lens-side cylindrical portion at the adjusted relative positions.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5 is a sectional view taken along line V-V in FIG. 4;

FIG. 6 is a schematic diagram showing an example of how a distal end of an optical fiber moves when the scanning endoscopic device according to the first embodiment is used to scan a subject;

FIG. 9 is a sectional view taken along line IX-IX in FIG. 7;

FIG. 10 is a schematic sectional view showing a state in which a fiber-side facing portion and a lens-side facing portion are in abutment with each other when a lens optical system is focused during the manufacture of the light irradiating device according to the first embodiment;

FIG. 13 is a schematic sectional view showing a state in which a fiber-side facing portion and a lens-side facing portion are in abutment with each other when a lens optical system is focused during the manufacture of the light irradiating device according to the second embodiment.

DETAILED DESCRIPTION OF THE INVENTION (First Embodiment)

A first embodiment of the present invention is described with reference to FIG. 1 to FIG. 9.

Figure 1:
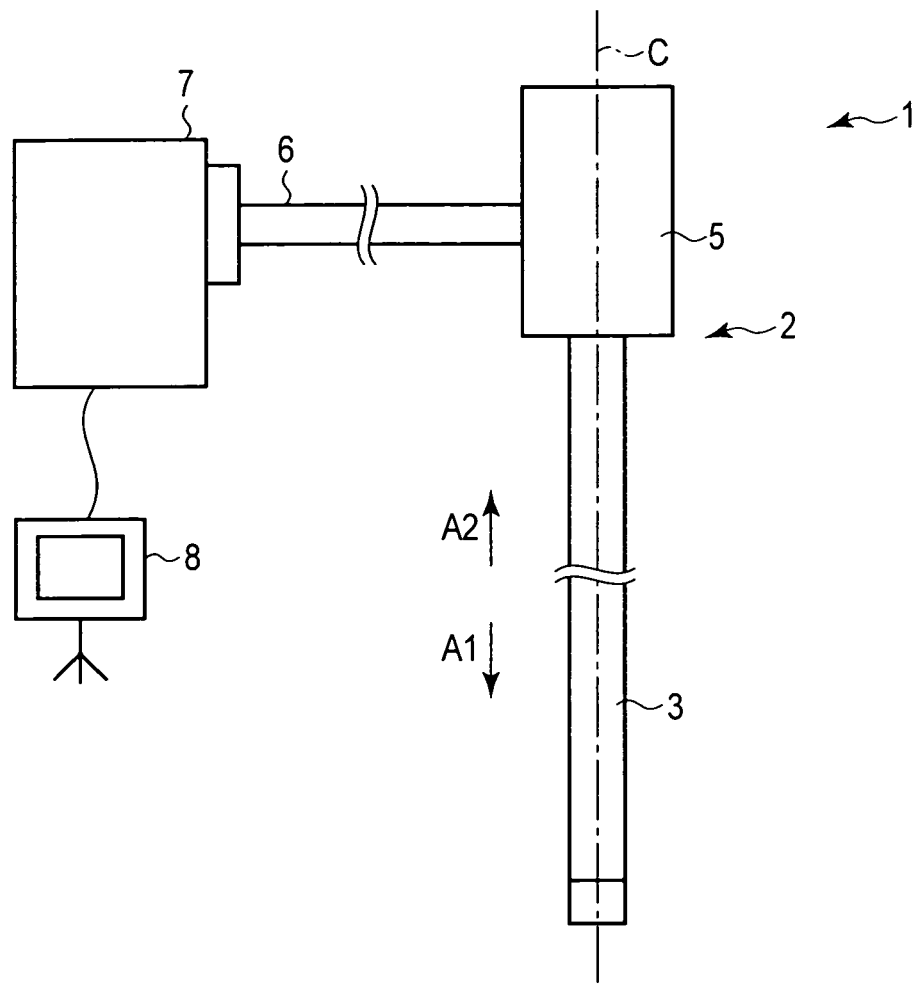
FIG. 1 is a schematic diagram showing a scanning endoscopic device according to a first embodiment of the present invention.
Figure 2:
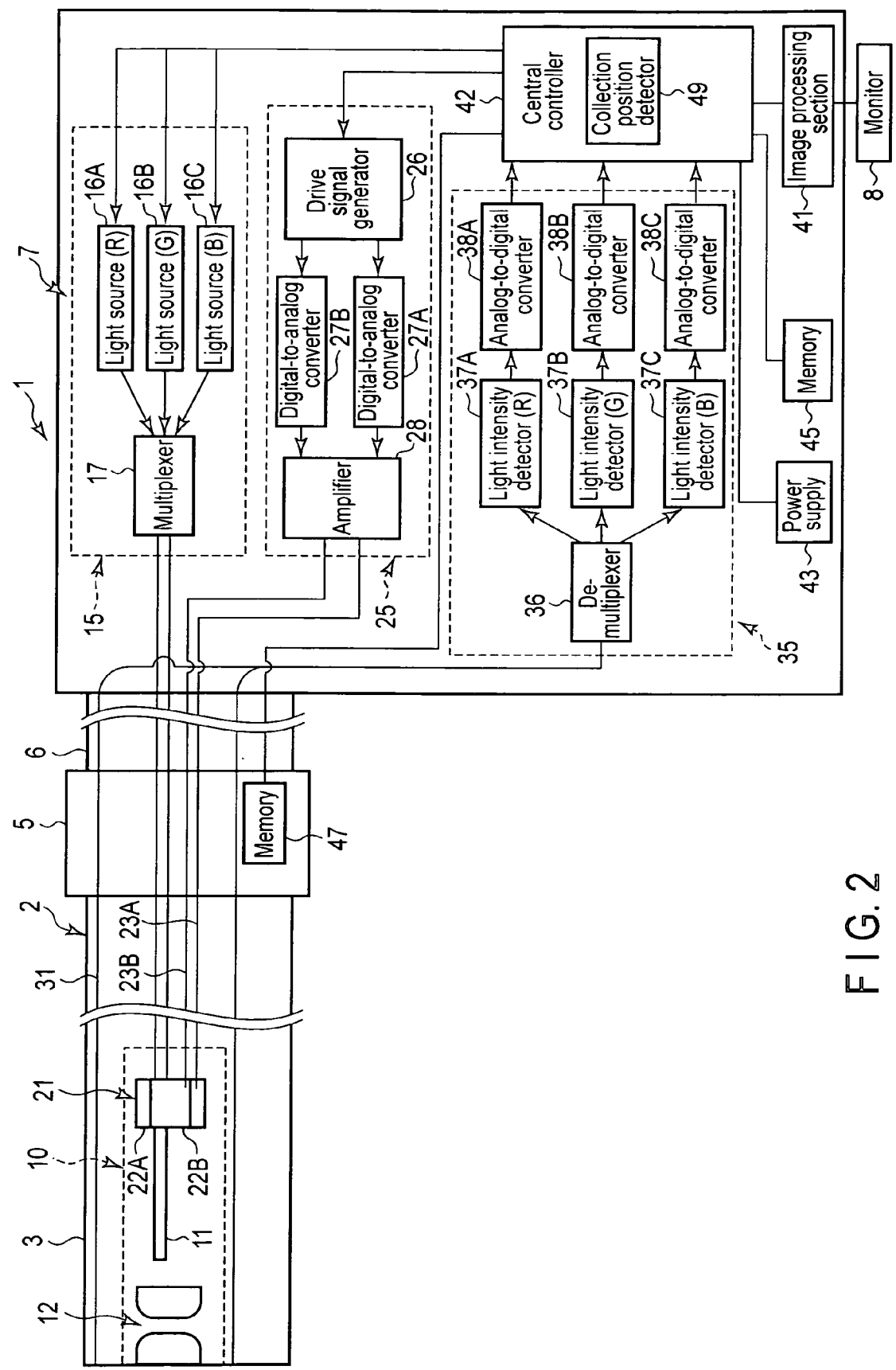
FIG. 2 is a schematic block diagram showing the scanning endoscopic device according to the first embodiment.

FIG. 1 and FIG. 2 are diagrams showing a scanning endoscopic device 1 according to the present embodiment. The scanning endoscopic device 1 is configured to scan a subject, and configured to generate an image of the subject. The scanning endoscopic device 1 has a longitudinal axis C. One of directions parallel to the longitudinal axis C is a distal direction (direction of an arrow A1 in FIG. 1), and the other of the directions parallel to the longitudinal axis is a proximal direction (direction of an arrow A2 in FIG. 1).

As shown in FIG. 1 and FIG. 2, the scanning endoscopic device 1 includes a scanning endoscope 2. The scanning endoscope 2 includes an insertion section 3 extending along the longitudinal axis C, and a holding section 5 provided to the proximal direction side of the insertion section 3. One end of a universal cord 6 is connected to the holding section 5. The other end of the universal cord 6 is connected to a control unit 7. The control unit 7 is electrically connected to a monitor 8 which is a display. A light irradiating device 10 configured to irradiate (apply) light to the subject is provided in the scanning endoscope 2.

Figure 3:
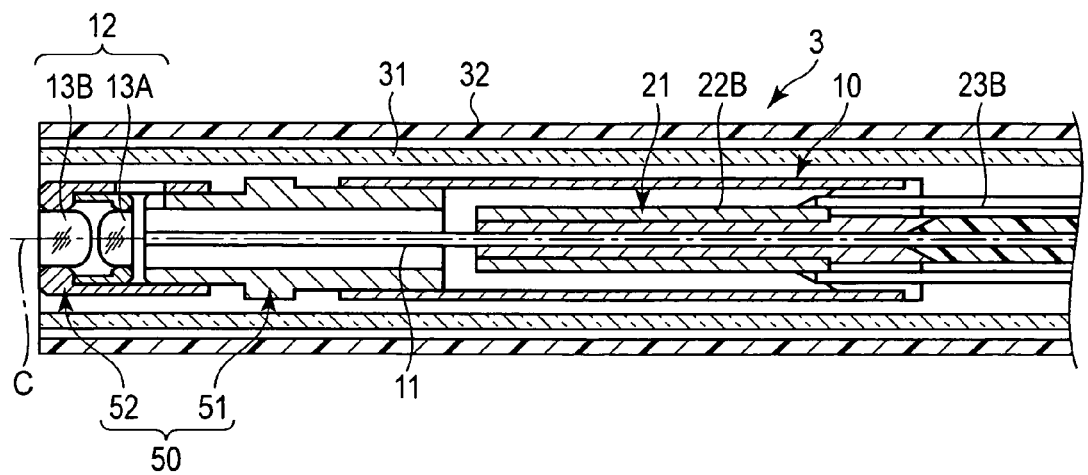
FIG. 3 is a schematic sectional view showing a configuration of a distal portion of a scanning endoscope according to the first embodiment.
Figure 4:
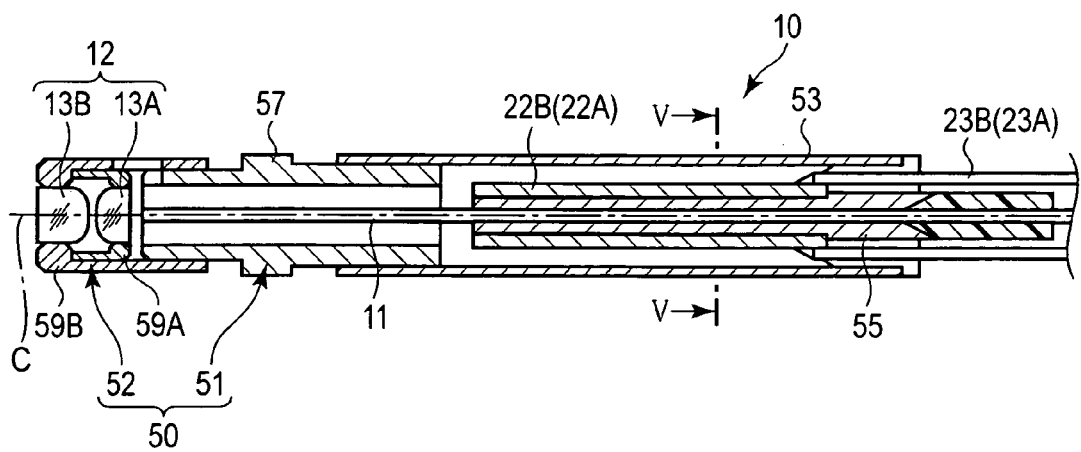
FIG. 4 is a schematic sectional view showing a configuration of a light irradiating device according to the first embodiment.

FIG. 3 is a diagram showing the configuration of the distal portion of the insertion section 3 of the scanning endoscope 2. FIG. 4 is a diagram showing the light irradiating device 10. As shown in FIG. 2 to FIG. 4, the light irradiating device 10 includes an optical fiber 11 extended along the longitudinal axis C in the insertion section 3. The optical fiber 11 is optically connected to a light generator 15 of the control unit 7 through an inside of the holding section 5 and an inside of the universal cord 6.

A lens optical system 12 is provided to the distal direction side of the optical fiber 11. The optical axis of the lens optical system 12 corresponds to the longitudinal axis C. The lens optical system 12 includes a first lens 13A, and a second lens 13B provided to the distal direction side of the first lens 13A.

Here, the first lens 13A is a lens (most-proximal lens) located on the most proximal direction side in the lens optical system 12. That is, a proximal end of the first lens 13A serves as a proximal end of the lens optical system 12. A distal end of the second lens 13B is located on a distal surface of the insertion section 3.

The light irradiating device 10 includes an actuator section 21. FIG. 5 is a sectional view taken along line V-V in FIG. 4. The actuator section 21 includes a piezoelectric element 22A configured to generate ultrasonic vibrations in X-directions (directions of arrows X in FIG. 5) perpendicular to the longitudinal axis C, and a piezoelectric element 22B configured to generate ultrasonic vibrations in Y-directions (directions of arrows Y in FIG. 5) perpendicular to the longitudinal axis C and perpendicular to the X-directions. As shown in FIG. 2, one end of an electrical wiring line 23A is connected to piezoelectric element 22A, and one end of an electrical wiring line 23B is connected to piezoelectric element 22B. Each of electrical wiring lines 23A and 23B has the other end connected to a drive current supplier 25 of the control unit 7 through the inside of the holding section 5 and the inside of the universal cord 6.

As shown in FIG. 2 and FIG. 3, a cylindrical light guide 31 is attached to an outer peripheral direction side of the light irradiating device 10. The light guide 31 is extended from the distal surface of the insertion section 3 along the longitudinal axis C. The light guide 31 is optically connected to a light detector (photodetector) 35 of the control unit 7 through the inside of the holding section 5 and the inside of the universal cord 6.

In the insertion section 3 of the scanning endoscope 2, an envelope tube 32 is attached to the outer peripheral direction side of the light guide 31. A part of an outer surface of the scanning endoscope 2 is formed by the envelope tube 32. In the insertion section 3, the light irradiating device 10 and the light guide 31 are contained in the envelope tube 32.

As shown in FIG. 2, the control unit 7 includes an image processing section 41 such as an image processor configured to process a generation of images, and a central controller 42 configured to control the overall control unit 7. The image processing section 41 is electrically connected to the monitor 8. The control unit 7 also includes a power supply 43 such as a battery configured to supply electricity to the overall control unit 7, and a memory 45. For example, various kinds of specification information (spec information) regarding the light generator 15, the drive current supplier 25, and the light detector 35, and a calculation processing program performed in the central controller 42 are recorded in the memory 45. A memory 47 is provided in the holding section 5 of the scanning endoscope 2. The memory 47 is electrically connected to the central controller 42 of the control unit 7. For example, various kinds of specification information (spec information) regarding the scanning endoscope 2 are recorded in the memory 47.

Here, the configuration to scan the subject by the scanning endoscopic device 1 to generate an image of the subject is described. The light generator 15 includes three light sources 16A to 16C, and a multiplexer 17. The emission of light from each of the light sources 16A to 16C is controlled by the central controller 42. The light sources 16A to 16C are configured to emit light of different wavelength band with respect to one another. For example, the light source 16A emits light of red (R) wavelength band, the light source 16B emits light of green (G) wavelength band, and the light source 16C emits light of blue (B) wavelength band. The multiplexer 17 is then configured to multiplex the light emitted from the light sources 16A to 16C so that white light is formed.

The multiplexed light is guided to the distal direction from the proximal direction by the optical fiber 11. The guided light is then emitted from the distal end of the optical fiber 11. The light emitted from the optical fiber 11 is collected to the subject by the lens optical system 12. In the subject, the light is collected to one collection position (spot) by the lens optical system 12.

The drive current supplier 25 includes a drive signal generator 26, two digital-to-analog (D/A) converters 27A and 27B, and an amplifier 28. The drive signal generator 26 is configured to generate a digital drive signal which generates ultrasonic vibrations in the X-directions, and configured to output the digital drive signal to digital-to-analog converter 27A. The drive signal generator 26 is also configured to generate a digital drive signal which generates ultrasonic vibrations in the Y-directions, and configured to output the digital drive signal to digital-to-analog converter 27B. The output of each of the digital drive signals from the drive signal generator 26 is controlled by the central controller 42.

Digital-to-analog converter 27A is configured to convert the digital drive signal to a drive current. The drive current is then amplified by the amplifier 28, and the drive current is supplied to piezoelectric element 22A through electrical wiring line 23A. Digital-to-analog converter 27B is configured to convert the digital drive signal to a drive current. The drive current is then amplified by the amplifier 28, and the drive current is supplied to piezoelectric element 22B through electrical wiring line 23B. Ultrasonic vibrations in the X-directions are generated by the supply of the drive current to piezoelectric element 22A. Ultrasonic vibrations in the Y-directions are generated by the supply of the drive current to piezoelectric element 22B. When the ultrasonic vibrations are generated by piezoelectric elements 22A and 22B of the actuator section 21, vibrations are transmitted to the optical fiber 11, and the optical fiber 11 is driven.

As the optical fiber 11 is driven, a distal end of the optical fiber 11 moves on a substantially planar surface perpendicular to the longitudinal axis C. The movement of the distal end of the optical fiber 11 is adjusted by the control of the output of each digital drive signal in the drive signal generator 26. As shown by way of example in FIG. 6, the distal end of the optical fiber 11 is adjusted to spirally move on the substantially planar surface perpendicular to the longitudinal axis C. In response to the movement of the distal end of the optical fiber 11, the emission position of the light from the optical fiber 11 changes with time. As a result, the position in the subject where the light is collected by the lens optical system 12 changes with time. In this way, light is irradiated (applied) to the subject from the light irradiating device 10. Here, the movement on the substantially planar surface means that the distal end of the optical fiber 11 does not necessarily move strictly on the plane but the movement amount of the distal end of the optical fiber 11 in directions parallel to the longitudinal axis C is small to the degree that allows the distal end of the optical fiber 11 to be regarded as moving on the plane.

The light irradiated (applied) to the collection position of the subject is reflected at the collection position. The light guide 31 then receives, with time, the light reflected at the collection position. The light received by the light guide 31 is guided to the light detector 35 through the light guide 31.

The light detector 35 includes a demultiplexer 36, three light intensity detectors 37A to 37C, and three analog-to-digital (A/D) converters 38A to 38C. The demultiplexer 36 is, for example, a dichroic mirror, and is configured to demultiplex the light guided by the light guide 31 into light of three different wavelength bands. For example, the demultiplexer 36 demultiplexes the guided light into a first spectrum of red (R) wavelength band, a second spectrum of green (G) wavelength band, and a third spectrum of blue (B) wavelength band.

The first spectrum is then guided to the light intensity detector 37A, and the intensity of the first spectrum is detected by the light intensity detector 37A. A current of a physical quantity based on the intensity of the first spectrum is then output to analog-to-digital converter 38A, and is converted to a digital signal by analog-to-digital converter 38A. The digital signal based on the intensity of the first spectrum is then transmitted to the central controller 42. In the light intensity detector 37B and analog-to-digital converter 38B, the intensity of the second spectrum is detected as in the light intensity detector 37A and analog-to-digital converter 38A. The digital signal that indicates information based on the intensity of the second spectrum is then transmitted to the central controller 42. In the light intensity detector 37C and analog-to-digital converter 38C, the intensity of the third spectrum is detected as in the light intensity detector 37A and analog-to-digital converter 38A. The digital signal based on the intensity of the third spectrum is then transmitted to the central controller 42. In this way, the light detector 35 detects, with time, the kind and intensity of light guided by the light guide 31.

That is, when the scanning endoscopic device 1 observes a subject, the collection position in the subject changes with time. The kind and intensity of light reflected from the collection position which changes with time are then detected by the light detector (photodetector) 35. Thus, the subject is scanned.

The central controller 42 includes a collection position detector 49 which is configured to detect, with time, the position in the subject where the light is collected by the lens optical system 12. The collection position detector 49 detects the light collection position in the subject in accordance with the specification information regarding the scanning endoscope 2, the specification information regarding the control unit 7, and the digital drive signal from the drive signal generator 26. That is, the light collection position in the subject is detected in accordance with the drive current supplied to the actuator section 21 from the drive current supplier 25.

The image processing section 41 is configured to generate an image of the subject in accordance with the collection position detected with time and the kind and intensity of light reflected at the collection position detected with time. The generated image is then displayed on the monitor 8.

As shown in FIG. 4, the light irradiating device 10 includes a cylindrical unit 50. The cylindrical unit 50 is provided coaxially with the longitudinal axis C. The cylindrical unit 50 includes a fiber-side cylindrical portion 51 to which the optical fiber 11 is attached, and a lens-side cylindrical portion 52 to which the lens optical system 12 is fixed.

The fiber-side cylindrical portion 51 includes an actuator accommodating cylinder 53 in which the actuator section 21 is accommodated. A connection member 55 through which the optical fiber 11 is inserted is attached to the actuator accommodating cylinder 53, for example, by adhesion. The optical fiber 11 is attached to the connection member 55 in a state that the optical fiber 11 is inserted through the connection member 55. In this way, the optical fiber 11 is attached to the actuator accommodating cylinder 53 (fiber-side cylindrical portion 51) so that the movement of the optical fiber 11 along the longitudinal axis C is regulated and so that the distal end of the optical fiber 11 is movable perpendicularly to the longitudinal axis C.

Piezoelectric elements 22A and 22B are fixed to an outer circumferential portion of the connection member 55. Ultrasonic vibrations generated in piezoelectric elements 22A and 22B are transmitted to the optical fiber 11 via the connection member 55. As a result, the optical fiber 11 is driven, and the distal end of the optical fiber 11 moves on the substantially planar surface perpendicular to the longitudinal axis C.

The fiber-side cylindrical portion 51 includes a fiber distal end accommodating cylinder 57 provided to the distal direction side of the actuator accommodating cylinder 53. The fiber distal end accommodating cylinder 57 is fixed to the actuator accommodating cylinder 53, for example, by adhesion. The distal end of the optical fiber 11 is accommodated in the fiber distal end accommodating cylinder 57.

The lens-side cylindrical portion 52 includes a first lens frame (lens frame) 59A to which the first lens 13A (most-proximal lens) is fixed, and a second lens frame 59B to which the second lens 13B is fixed. The first lens frame 59A is fixed to the second lens frame 59B, for example, by adhesion. The fiber distal end accommodating pipe 57 is fixed to the second lens frame 59B, for example, by adhesion.

Figure 7:
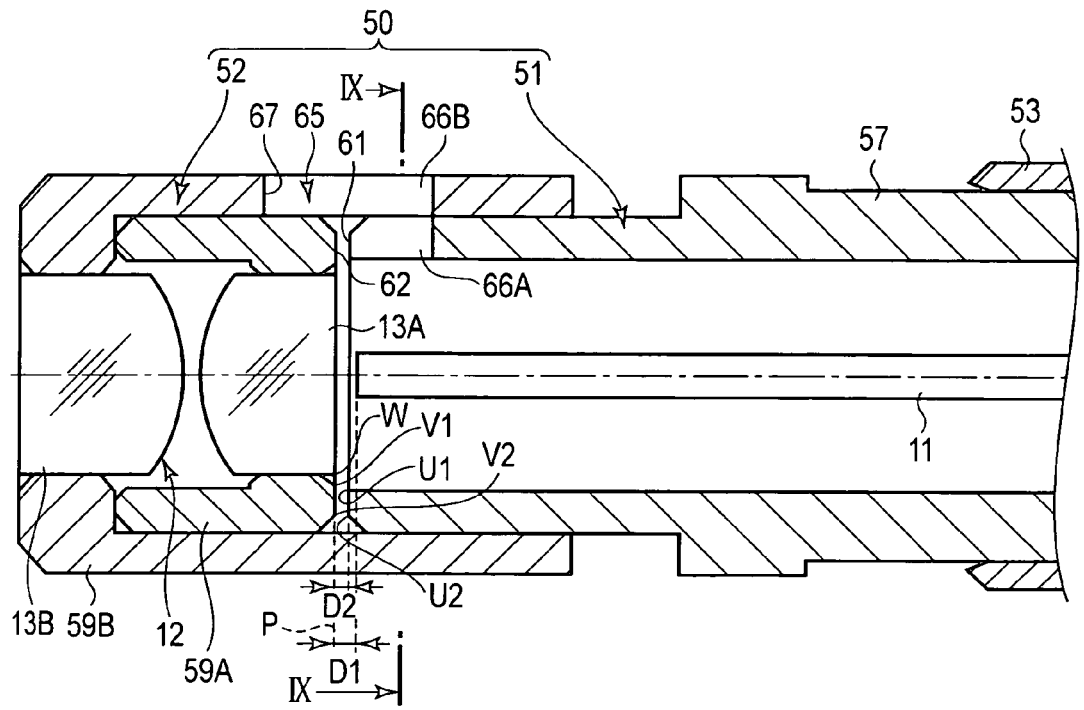
FIG. 7 is a schematic sectional view showing a configuration of a distal portion of the light irradiating device according to the first embodiment.
Figure 8:
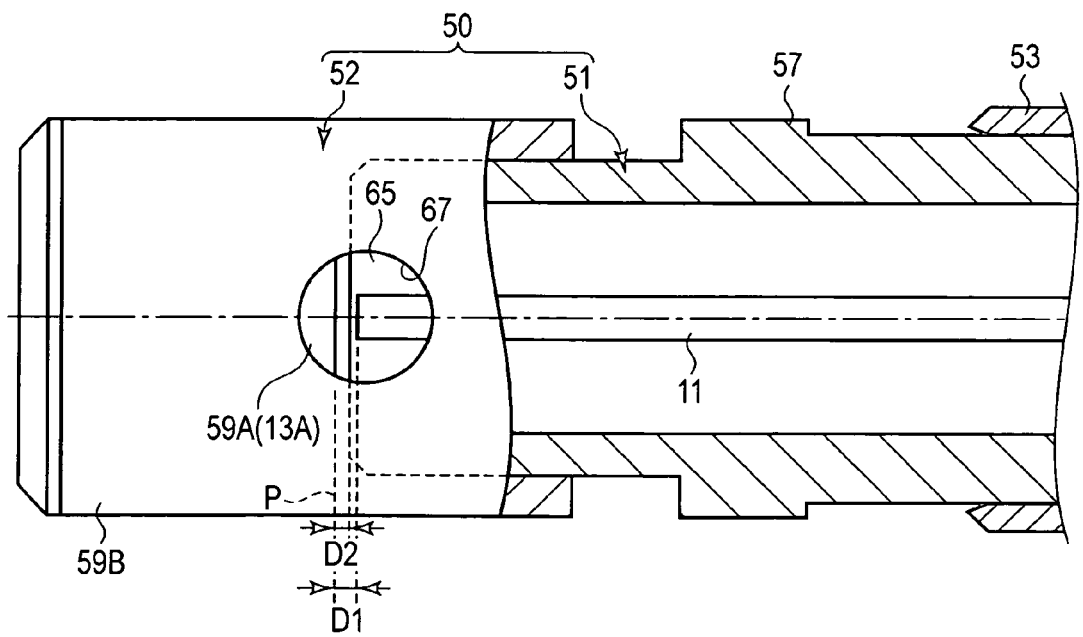
FIG. 8 is a schematic plan view partly in section showing the configuration of the distal portion of the light irradiating device according to the first embodiment.

FIG. 7 and FIG. 8 are diagrams showing the configuration of the distal portion of the light irradiating device 10. FIG. 9 is a sectional view taken along line IX-IX in FIG. 7. As shown in FIG. 7 to FIG. 9, a fiber-side facing portion 61 is provided at a distal end of the fiber distal end accommodating cylinder 57 (fiber-side cylindrical portion 51). The fiber-side facing portion 61 faces in the distal direction. The fiber-side facing portion 61 has an inner peripheral end U1 and an outer peripheral end U2. The distal end of the optical fiber 11 is located to the proximal direction side of the fiber-side facing portion 61.

A lens-side facing portion 62 is provided at the proximal end of the first lens frame 59A (lens-side cylindrical portion 52). The lens-side facing portion 62 faces in the proximal direction, and faces the fiber-side facing portion 61. The lens-side facing portion 62 has an inner peripheral end V1 and an outer peripheral end V2. The inner peripheral end V1 of the lens-side facing portion 62 is located to the inner peripheral direction side of the outer peripheral end U2 of the fiber-side facing portion 61. The outer peripheral end V2 of the lens-side facing portion 62 is located to the outer peripheral direction side of the inner peripheral end U1 of the fiber-side facing portion 61.

The first lens 13A is attached to the first lens frame 59A so that the lens-side facing portion 62 and a proximal end of the first lens 13A which is the most-proximal lens are located on the same reference plane P perpendicular to the longitudinal axis C. That is, the proximal end of the first lens frame 59A is located on the reference plane P. A dimension between the distal end of the optical fiber 11 and the reference plane P along the longitudinal axis C is a first dimension D1. Therefore, the proximal end of the first lens 13A (the proximal end of the lens optical system 12) is located apart from the distal end of the optical fiber 11 by the first dimension D1 in the distal direction. When the proximal end of the lens optical system 12 is located apart from the distal end of the optical fiber 11 by the first dimension D1 in the distal direction, the in-focus condition in which the light emitted from the optical fiber 11 is collected to the subject by the lens optical system 12 is formed, and the lens optical system 12 is focused with respect to the light emitted from the optical fiber 11. Here, the first dimension D1 is, for example, 0.2 mm or less, and is small, and the first dimension D1 is about 0.04 to 0.06 mm in effect.

As described above, the distal end of the optical fiber 11 is located to the proximal direction side of the fiber-side facing portion 61, and the lens-side facing portion 62 and the proximal end of the first lens 13A are located on the same reference plane P. Thus, a dimension between the fiber-side facing portion 61 and the reference plane P along the longitudinal axis C is a second dimension D2 smaller than the first dimension D1. That is, the lens-side facing portion 62 is located apart from the fiber-side facing portion 61 by the second dimension D2 smaller than the first dimension D1 in the distal direction. Here, the second dimension D2 is about 0.02 to 0.04 mm.

The first lens 13A has an outer peripheral end W. The inner peripheral end U1 of the fiber-side facing portion 61 is located to the outer peripheral direction side of the outer peripheral end W of the first lens 13A.

A window 65 is provided in the cylindrical unit 50 along diametrical directions from an outer portion to an inner portion. The window 65 is configured by a hole 66A formed in the fiber distal end accommodating cylinder 57 and a hole 66B formed in the second lens frame 59B. That is, a window defining portion 67 which defines the window 65 is provided in the fiber distal end accommodating cylinder 57 and the second lens frame 59B. The proximal end of the lens optical system 12 (the proximal end of the first lens 13A) and the distal end of the optical fiber 11 are located between a distal end of the window 65 and a proximal end of the window 65 in the directions parallel to the longitudinal axis C. Therefore, the proximal end of the lens optical system 12 and the distal end of the optical fiber 11 can be visually recognized from the outside of the cylindrical unit 50 through the window 65.

Now, manufacturing methods of the light irradiating device 10 and the scanning endoscope 2 are described. In the following explanation, a condition in which the light irradiating device 10 is completed, that is, a condition in which the proximal end of the lens optical system 12 is located apart from the distal end of the optical fiber 11 by the first dimension D1 in the distal direction is an in-focus condition. In the in-focus condition, the light emitted from the optical fiber 11 is collected to the subject by the lens optical system 12. Moreover, in the in-focus condition, the fiber-side cylindrical portion 51 and the lens-side cylindrical portion 52 are coaxial with the longitudinal axis C, and the optical axis of the lens optical system 12 corresponds to the longitudinal axis C.

When the light irradiating device 10 is manufactured, the fiber-side cylindrical portion 51 is formed, and the optical fiber 11 is attached to the fiber-side cylindrical portion 51. At the same time, the optical fiber 11 extended along the longitudinal axis C is inserted through the connection member 55 to attach the optical fiber 11 to the connection member 55. The connection member 55 and the actuator accommodating cylinder 53 are then disposed coaxially with the longitudinal axis C, and the connection member 55 is attached to the actuator accommodating cylinder 53, for example, by adhesion. The actuator accommodating cylinder 53 and the fiber distal end accommodating cylinder 57 are then disposed coaxially with the longitudinal axis C, and the fiber distal end accommodating cylinder 57 is fixed to the actuator accommodating cylinder 53, for example, by adhesion. In this way, the fiber-side cylindrical portion 51 is formed, and the optical fiber 11 is attached to the fiber-side cylindrical portion 51.

At the same time, the optical fiber 11 is attached to the fiber-side cylindrical portion 51 so that the movement of the optical fiber 11 along the longitudinal axis C is regulated and so that the distal end of the optical fiber 11 is movable perpendicularly to the longitudinal axis C. The distal end of the optical fiber 11 is accommodated in the fiber distal end accommodating cylinder 57 of the fiber-side cylindrical portion 51.

The fiber-side facing portion 61 is formed at the distal end of the fiber distal end accommodating cylinder 57. The fiber-side facing portion 61 is formed to face in the distal direction in the in-focus condition. The distal end of the optical fiber 11 is located to the proximal direction side of the fiber-side facing portion 61. As the fiber-side facing portion 61 is provided at the distal end of the fiber distal end accommodating cylinder 57, the fiber-side facing portion 61 can be easily formed.

In the manufacture of the light irradiating device 10, the lens-side cylindrical portion 52 is formed, and the lens optical system 12 is fixed to the lens-side cylindrical portion 52. The first lens (most-proximal lens) 13A is fixed to the first lens frame 59A, and the second lens 13B is fixed to the second lens frame 59B. The first lens frame 59A and the second lens frame 59B are then disposed coaxially with the optical axis of the lens optical system 12, and the first lens frame 59A is fixed to the second lens frame 59B, for example, by adhesion. In this way, the lens-side cylindrical portion 52 is formed, and the lens optical system 12 is fixed to the lens-side cylindrical portion 52.

The lens-side facing portion 62 is formed at the proximal end of the first lens frame 59A. The lens-side facing portion 62 is formed to face in the proximal direction in the in-focus condition. The lens-side facing portion 62 is also formed to face the fiber-side facing portion 61 apart from the fiber-side facing portion 61 by the second dimension D2 smaller than the first dimension D1 in the distal direction in the in-focus condition. Moreover, the lens-side facing portion 62 is formed so that the inner peripheral end V1 of the lens-side facing portion 62 is located to the inner peripheral direction side of the outer peripheral end U2 of the fiber-side facing portion 61 and so that the outer peripheral end V2 of the lens-side facing portion 62 is located to the outer peripheral direction side of the inner peripheral end U1 of the fiber-side facing portion 61 in the in-focus condition. As the lens-side facing portion 62 is provided at the proximal end of the first lens frame 59A, the lens-side facing portion 62 can be easily formed. The first lens 13A is fixed so that the inner peripheral end U1 of the fiber-side facing portion 61 is located to the outer peripheral direction side of the outer peripheral end W of the first lens 13A in the in-focus condition.

At the same time, the lens-side facing portion 62 and the proximal end of the first lens 13A are located on the same plane perpendicular to the optical axis of the lens optical system 12. That is, the lens-side facing portion 62 is formed in the first lens frame 59A so that the lens-side facing portion 62 and the proximal end of the first lens (most-proximal lens) 13A are located on the same reference plane P perpendicular to the longitudinal axis C in the in-focus condition. As the lens-side facing portion 62 and the proximal end of the lens optical system 12 are located on the same plane perpendicular to the optical axis (longitudinal axis C), the position at which the lens optical system 12 is fixed to the lens-side cylindrical portion 52 is adjusted simply by the adjustment of the position of the proximal end of the lens optical system 12 to the position of the lens-side facing portion 62. Thus, the lens optical system 12 is more easily fixed to the lens-side cylindrical portion 52 than when the lens-side facing portion 62 and the proximal end of the lens optical system 12 are located apart from each other in the directions parallel to the longitudinal axis C.

Furthermore, the lens-side facing portion 62 and the proximal end of the lens optical system 12 are located on the same reference plane P perpendicular to the longitudinal axis C. Therefore, in the formation of the fiber-side cylindrical portion 51 and the attachment of the optical fiber 11 to the fiber-side cylindrical portion 51, it is not necessary to consider the difference of position between the lens-side facing portion 62 and the proximal end of the lens optical system 12 in the directions parallel to the longitudinal axis C. That is, the formation position of the fiber-side facing portion 61 and the position of the distal end of the optical fiber 11 are determined without the consideration of the difference of position between the lens-side facing portion 62 and the proximal end of the lens optical system 12 in the directions parallel to the longitudinal axis C. Thus, the formation of the fiber-side facing portion 61 in the fiber-side cylindrical portion 51 and the positional adjustment of the distal end of the optical fiber 11 are easier than when the lens-side facing portion 62 and the proximal end of the lens optical system 12 are located apart from each other in the directions parallel to the longitudinal axis C. Consequently, the formation of the fiber-side cylindrical portion 51 and the attachment of the optical fiber 11 to the fiber-side cylindrical portion 51 are easier than when the lens-side facing portion 62 and the proximal end of the lens optical system 12 are located apart from each other in the directions parallel to the longitudinal axis C.

When the fiber-side cylindrical portion 51 is formed, the hole 66A is formed in the fiber distal end accommodating cylinder 57. When the lens-side cylindrical portion 52 is formed, the hole 66B is formed in the second lens frame 59B. That is, the holes 66A and 66B are formed in the cylindrical unit 50 along the diametrical directions from the outer portion to the inner portion. In the in-focus condition, the window 65 is configured by the holes 66A and 66B. The holes 66A and 66B are formed so that the proximal end of the lens optical system 12 (the proximal end of the first lens 13A) and the distal end of the optical fiber 11 are located between the distal end and the proximal end of the window 65 in the directions parallel to the longitudinal axis C in the in-focus condition.

In the manufacture of the light irradiating device 10, the actuator section 21 is formed. At the same time, piezoelectric elements 22A and 22B are fixed to the outer peripheral portion of the connection member 55. One end of electrical wiring line 23A is connected to piezoelectric element 22A, and one end of electrical wiring line 23B is connected to piezoelectric element 22B. Ultrasonic vibrations are generated in piezoelectric elements 22A and 22B by the supply of the drive current. The generated ultrasonic vibrations are transmitted to the optical fiber 11 via the connection member 55. As a result, the optical fiber 11 is driven, and the distal end of the optical fiber 11 moves on the substantially planar surface perpendicular to the longitudinal axis C. In this way, the actuator section 21 is formed whereby the optical fiber 11 can be driven so that the distal end of the optical fiber 11 moves on the substantially planar surface perpendicular to the longitudinal axis C. The actuator section 21 is formed to change, with time, the position in the subject where the light is collected by the lens optical system 12 in response to the movement of the distal end of the optical fiber 11 in the in-focus condition.

In the manufacture of the light irradiating device 10, the relative positions of the fiber-side cylindrical portion 51 and the lens-side cylindrical portion 52 in the directions parallel to the longitudinal axis C are adjusted to positions in the in-focus condition. At the same time, the lens optical system 12 (first lens 13A) fixed to the lens-side cylindrical portion 52 is located to the distal direction side of the optical fiber 11 attached to the fiber-side cylindrical portion 51. The optical axis of the lens optical system 12 is then brought into correspondence the longitudinal axis C. That is, the fiber-side cylindrical portion 51 and the lens-side cylindrical portion 52 are disposed coaxially with the longitudinal axis C. In this condition, the fiber-side cylindrical portion 51 and the lens-side cylindrical portion 52 are moved relative to each other in the directions parallel to the longitudinal axis C. In this way, the relative positions of the fiber-side cylindrical portion 51 and the lens-side cylindrical portion 52 in the directions parallel to the longitudinal axis C are adjusted to positions in the in-focus condition. The dimension between the distal end of the optical fiber 11 and the proximal end of the lens optical system 12 is adjusted to the first dimension D1 by the adjustment of the relative positions of the fiber-side cylindrical portion 51 and the lens-side cylindrical portion 52. That is, the lens optical system 12 is focused with respect to the light emitted from the optical fiber 11.

Here, in the in-focus condition, the proximal end of the lens optical system 12 (the proximal end of the first lens 13A) and the distal end of the optical fiber 11 are located between the distal end and the proximal end of the window 65 in the directions parallel to the longitudinal axis C. Thus, the proximal end of the lens optical system 12 and the distal end of the optical fiber 11 can be visually recognized through the window 65 in focusing. Therefore, the dimension between the distal end of the optical fiber 11 and the proximal end of the lens optical system 12 is easily adjusted. Moreover, it is not necessary to scan the subject and generate the image of the subject by using the light guide 31, the light detector 35, and the image processing section 41 in addition to the light irradiating device 10, and not necessary to focus the lens optical system 12 while visually recognizing the generated image of the subject. As a result, the focusing of the lens optical system 12 is easier.

In the in-focus condition, the first dimension D1 between the distal end of the optical fiber 11 and the proximal end of the lens optical system 12 is, for example, 0.2 mm or less (0.04 to 0.06 mm in effect), and is small. The second dimension D2 between the fiber-side facing portion 61 and the lens-side facing portion 62 is 0.02 to 0.04 mm, and is small. Therefore, when the lens optical system 12 is focused with respect to the light emitted from the optical fiber 11, the dimension between the fiber-side facing portion 61 and the lens-side facing portion 62 in the directions parallel to the longitudinal axis C may be zero.

In focusing, the inner peripheral end V1 of the lens-side facing portion 62 is located to the inner peripheral direction side of the outer peripheral end U2 of the fiber-side facing portion 61, and the outer peripheral end V2 of the lens-side facing portion 62 is located to the outer peripheral direction side of the inner peripheral end U1 of the fiber-side facing portion 61. Thus, when the dimension between the fiber-side facing portion 61 and the lens-side facing portion 62 in the directions parallel to the longitudinal axis C is zero, the fiber-side facing portion 61 and the lens-side facing portion 62 are in abutment with each other.

FIG. 10 is a diagram showing a state in which the fiber-side facing portion 61 and the lens-side facing portion 62 are in abutment with each other when the lens optical system 12 is focused with respect to the light emitted from the optical fiber 11. As described above, the distal end of the optical fiber 11 is located to the proximal direction side of the fiber-side facing portion 61, and the proximal end of the lens optical system 12 and the lens-side facing portion 62 are located on the same reference plane P perpendicular to the longitudinal axis C. Thus, as shown in FIG. 10, the distal end of the optical fiber 11 and the proximal end of the lens optical system 12 (the proximal end of the first lens 13A) are not in contact with each other when the fiber-side facing portion 61 and the lens-side facing portion 62 are in abutment with each other in focusing. The movement of the fiber-side cylindrical portion 51 in the distal direction relative to the lens-side cylindrical portion 52 is regulated by the abutment of the fiber-side facing portion 61 and the lens-side facing portion 62. That is, in focusing, the fiber-side cylindrical portion 51 cannot move in the distal direction relative to the lens-side cylindrical portion 52 from the condition in which the fiber-side facing portion 61 and the lens-side facing portion 62 are in abutment with each other. Therefore, in focusing, the contact between the distal end of the optical fiber 11 and the proximal end of the lens optical system 12 is prevented, and the damage to the optical fiber 11 and the lens optical system 12 is effectively prevented. As the contact between the distal end of the optical fiber 11 and the proximal end of the lens optical system 12 is prevented by the fiber-side facing portion 61 and the lens-side facing portion 62, the focusing of the lens optical system 12 is easy.

The inner peripheral end U1 of the fiber-side facing portion 61 is located to the outer peripheral direction side of the outer peripheral end W of the first lens 13A. Therefore, the fiber-side facing portion 61 (the fiber-side cylindrical portion 51) does not contact the first lens 13A when the fiber-side facing portion 61 and the lens-side facing portion 62 are in abutment with each other in focusing. As a result, damage to the first lens 13A is more effectively prevented.

After the relative positions of the fiber-side cylindrical portion 51 and the lens-side cylindrical portion 52 in the directions parallel to the longitudinal axis C are adjusted to positions in the in-focus condition, the fiber-side cylindrical portion 51 is fixed to the lens-side cylindrical portion 52 at the adjusted relative positions, for example, by adhesion. In this way, the light irradiating device 10 is formed.

When the scanning endoscope 2 is formed, the light guide 31 is attached to the outer peripheral direction side of the completed light irradiating device 10. The envelope tube 32 is then attached to the outer peripheral direction side of the light guide 31. The envelope tube 32 is attached so that the light irradiating device 10 and the light guide 31 are contained therein, and the envelope tube 32 forms a part of the outer surface of the scanning endoscope 2. In this way, the scanning endoscope 2 is formed.

Accordingly, the light irradiating device 10 of the scanning endoscopic device 1 having the configuration described above and the manufacturing method of the same have the following advantageous effects. That is, in the light irradiating device 10, the proximal end of the lens optical system 12 (the proximal end of the first lens 13A) and the distal end of the optical fiber 11 are located between the distal end and the proximal end of the window 65 in the directions parallel to the longitudinal axis C. Thus, in the focusing of the lens optical system 12 during the manufacturing of the light irradiating device 10, the proximal end of the lens optical system 12 and the distal end of the optical fiber 11 can be visually recognized through the window 65. Therefore, the dimension between the distal end of the optical fiber 11 and the proximal end of the lens optical system 12 can be easily adjusted in focusing. Moreover, it is not necessary to scan the subject and generate the image of the subject by using the light guide 31, the light detector 35, and the image processing section 41 in addition to the light irradiating device 10, and not necessary to focus the lens optical system 12 while visually recognizing the generated image of the subject. Thus, the focusing of the lens optical system 12 can be easy. As a result, costs can be reduced in the manufacture of the light irradiating device 10, and the light irradiating device 10 can be manufactured without much time required.

In the light irradiating device 10, the inner peripheral end V1 of the lens-side facing portion 62 is located to the inner peripheral direction side of the outer peripheral end U2 of the fiber-side facing portion 61, and the outer peripheral end V2 of the lens-side facing portion 62 is located to the outer peripheral direction side of the inner peripheral end U1 of the fiber-side facing portion 61. Thus, when the dimension between the fiber-side facing portion 61 and the lens-side facing portion 62 in the directions parallel to the longitudinal axis C is zero in the focusing of the lens optical system 12, the fiber-side facing portion 61 and the lens-side facing portion 62 are in abutment with each other. Moreover, in the light irradiating device 10, the second dimension D2 between the fiber-side facing portion 61 and the lens-side facing portion 62 is smaller than the first dimension D1 between the distal end of the optical fiber 11 and the proximal end of the lens optical system 12. Thus, the distal end of the optical fiber 11 and the proximal end of the lens optical system 12 (the proximal end of the first lens 13A) are not in contact with each other when the fiber-side facing portion 61 and the lens-side facing portion 62 are in abutment with each other in focusing. In focusing, the fiber-side cylindrical portion 51 cannot move in the distal direction relative to the lens-side cylindrical portion 52 from a condition in which the fiber-side facing portion 61 and the lens-side facing portion 62 are in abutment with each other. Therefore, in focusing, the contact between the distal end of the optical fiber 11 and the proximal end of the lens optical system 12 is prevented, and the damage to the optical fiber 11 and the lens optical system 12 is effectively prevented. As the contact between the distal end of the optical fiber 11 and the proximal end of the lens optical system 12 is prevented by the fiber-side facing portion 61 and the lens-side facing portion 62, the focusing of the lens optical system 12 is easy. Consequently, costs can be reduced in the manufacture of the light irradiating device 10, and the light irradiating device 10 can be manufactured without much time required.

(Modifications)

Figure 11:
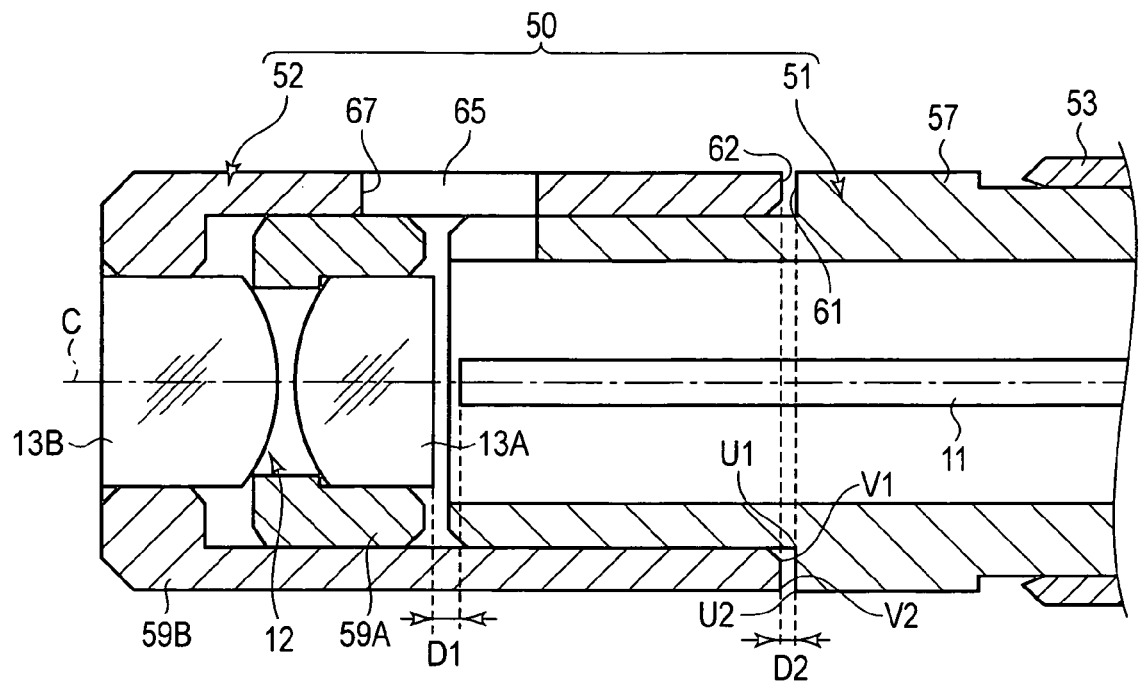
FIG. 11 is a schematic sectional view showing a configuration of a distal portion of a light irradiating device according to a second embodiment of the present invention.
Figure 12:
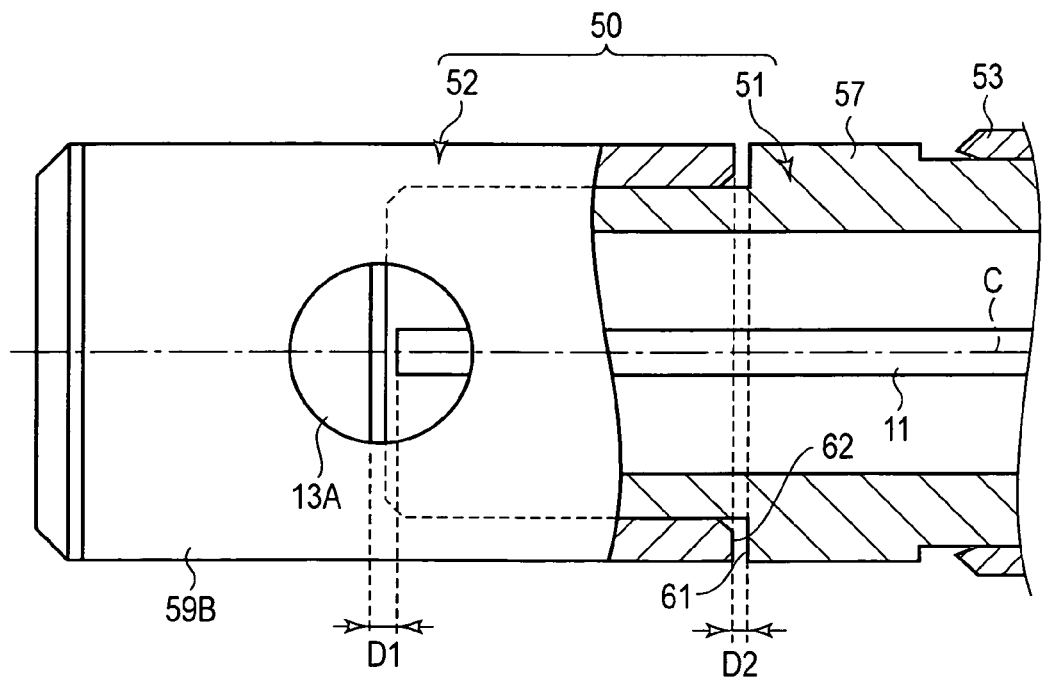
FIG. 12 is a schematic plan view partly in section showing the configuration of the distal portion of the light irradiating device according to the second embodiment.

In the first embodiment, the lens-side facing portion 62 and the proximal end of the lens optical system 12 (the proximal end of the first lens 13A) are located on the same reference plane P perpendicular to the longitudinal axis. However, this is not a limitation. For example, as in a modification shown in FIG. 11 and FIG. 12, the proximal end of the lens optical system 12 and the lens-side facing portion 62 may be located apart from each other in the directions parallel to the longitudinal axis C. In the present modification, the lens-side facing portion 62 is provided at a proximal end of the second lens frame 59B of the lens-side cylindrical portion 52, and the lens-side facing portion 62 is located to the proximal direction side of the proximal end of the lens optical system 12. The proximal end of the lens optical system 12 is located to the proximal direction side of the proximal end of the first lens frame 59A. As in the first embodiment, the lens-side facing portion 62 faces in the proximal direction, and has the inner peripheral end V1 and the outer peripheral end V2.

In the present modification, the fiber-side facing portion 61 is not provided at the distal end of the fiber distal end accommodating cylinder 57 but is provided in an intermediate portion of the fiber distal end accommodating cylinder 57 in the directions parallel to the longitudinal axis C. As in the first embodiment, the fiber-side facing portion 61 faces in the distal direction, and has the inner peripheral end U1 and the outer peripheral end U2. The distal end of the optical fiber 11 is located to the proximal direction side of the distal end of the fiber distal end accommodating cylinder 57.

In the present modification as well, the window 65 is defined by the window defining portion 67 along the diametrical directions from the outer portion to the inner portion of the cylindrical unit 50, as in the first embodiment. The proximal end of the lens optical system 12 and the distal end of the optical fiber 11 are located between the distal end and the proximal end of the window 65 in the directions parallel to the longitudinal axis C. Therefore, in the focusing of the lens optical system 12 during the manufacture of the light irradiating device 10, the proximal end of the lens optical system 12 and the distal end of the optical fiber 11 can be visually recognized through the window 65.

In the present modification as well, the inner peripheral end V1 of the lens-side facing portion 62 is located to the inner peripheral direction side of the outer peripheral end U2 of the fiber-side facing portion 61, and the outer peripheral end V2 of the lens-side facing portion 62 is located to the outer peripheral direction side of the inner peripheral end U1 of the fiber-side facing portion 61, as in the first embodiment. When the dimension between the fiber-side facing portion 61 and the lens-side facing portion 62 in the directions parallel to the longitudinal axis C is zero in the focusing of the lens optical system 12, the fiber-side facing portion 61 and the lens-side facing portion 62 are in abutment with each other.

FIG. 13 is a diagram showing a state in which the fiber-side facing portion 61 and the lens-side facing portion 62 are in abutment with each other when the lens optical system 12 is focused with respect to the light emitted from the optical fiber 11. In the present modification as well, the second dimension D2 between the fiber-side facing portion 61 and the lens-side facing portion 62 is smaller than the first dimension D1 between the distal end of the optical fiber 11 and the proximal end of the lens optical system 12, as in the first embodiment. Thus, as shown in FIG. 13, the distal end of the optical fiber 11 and the proximal end of the lens optical system 12 (the proximal end of the first lens 13A) are not in contact with each other when the fiber-side facing portion 61 and the lens-side facing portion 62 are in abutment with each other in focusing. In focusing, the fiber-side cylindrical portion 51 cannot move in the distal direction relative to the lens-side cylindrical portion 52 from the condition in which the fiber-side facing portion 61 and the lens-side facing portion 62 are in abutment with each other. Therefore, in focusing, the contact between the distal end of the optical fiber 11 and the proximal end of the lens optical system 12 is prevented, and the damage to the optical fiber 11 and the lens optical system 12 is effectively prevented.

However, in the present modification, the lens-side facing portion 62 and the proximal end of the lens optical system 12 are located apart from each other in the directions parallel to the longitudinal axis C, in contrast with in the first embodiment. As the lens-side facing portion 62 and the proximal end of the lens optical system 12 are located apart from each other in the directions parallel to the longitudinal axis C, it is necessary to determine the formation position of the fiber-side facing portion 61 and the position of the distal end of the optical fiber 11 in consideration of the difference of position between the lens-side facing portion 62 and the proximal end of the lens optical system 12 in the directions parallel to the longitudinal axis C.

Although the actuator section 21 includes piezoelectric elements 22A and 22B in the first embodiment, this is not a limitation. For example, as in an unshown modification, the actuator section may include a permanent magnet and a coil. In the present modification, electromagnetic force is generated by a magnetic field of the permanent magnet and by the drive current supplied to the coil from the drive current supplier 25. The optical fiber 11 is driven by the electromagnetic force, and the distal end of the optical fiber 11 moves on the substantially planar surface perpendicular to the longitudinal axis C.

Although the lens optical system 12 includes the two lenses 13A and 13B in the first embodiment, the number of the lenses of the lens optical system 12 is not limited to two. Although one cylindrical light guide 31 is provided in the first embodiment, a plurality light guides which receive light reflected from the collection position of the subject with time may be arranged side by side in directions around the longitudinal axis.

Thus, the modifications described above show that in the present invention, the actuator section 21 has only to drive the optical fiber 11 so that the distal end of the optical fiber 11 moves on the substantially planar surface perpendicular to the longitudinal axis C. Moreover, the position in the subject where the light is collected by the lens optical system 12 has only to be changed with time.

Furthermore, the fiber-side facing portion 61 has only to be provided in the fiber-side cylindrical portion 51 to face in the distal direction. The lens-side facing portion 62 has only to be provided in the lens-side cylindrical portion 52 to face in the proximal direction. In this case, the proximal end of the lens optical system 12 is located apart from the distal end of the optical fiber 11 by the first dimension D1 in the distal direction. The lens-side facing portion 62 faces the fiber-side facing portion 61 apart from the fiber-side facing portion 61 by the second dimension D2 smaller than the first dimension D1 in the distal direction. The inner peripheral end V1 of the lens-side facing portion 62 is located to the inner peripheral direction side of the outer peripheral end U2 of the fiber-side facing portion 61, and the outer peripheral end V2 of the lens-side facing portion 62 is located to the outer peripheral direction side of the inner peripheral end U1 of the fiber-side facing portion 61.

The window defining portion 67 has only to define the window 65 along the diametrical directions from the outer portion to the inner portion of the cylindrical unit 50. The proximal end of the lens optical system 12 and the distal end of the optical fiber 11 have only to be located between the distal end and the proximal end of the window 65 in the directions parallel to the longitudinal axis C.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. A light irradiating device in a scanning endoscopic device which is configured to scan a subject to generate an image of the subject, the light irradiating device comprising:
   an optical fiber which is extended along an longitudinal axis, and which is configured to emit, from a distal end thereof, light guided from a proximal direction to a distal direction;
   a lens optical system which is disposed so that a proximal end thereof is located apart from the distal end of the optical fiber in directions parallel to the longitudinal axis, and which is configured to collect the light emitted from the optical fiber to the subject;
   a cylindrical unit, the cylindrical unit including a fiber-side cylindrical portion to which the optical fiber is attached so that the movement of the optical fiber along the longitudinal axis is regulated, and a lens-side cylindrical portion to which the lens optical system is fixed and which is provided coaxially with the fiber-side cylindrical portion;
   a fiber-side facing portion which is provided in the fiber-side cylindrical portion so that the fiber-side facing portion faces in the distal direction;

a lens-side facing portion which is provided in the lens-side cylindrical portion so that the lens-side facing portion faces in the proximal direction, and which faces the fiber-side facing portion apart from the fiber-side facing portion by a second dimension smaller than a first dimension between the distal end of the optical fiber and the proximal end of the lens optical system in the directions parallel to the longitudinal axis; and a window defining portion which defines a window provided along diametrical directions from an outer portion to an inner portion of the cylindrical unit, the window defining portion defining the window so that the proximal end of the lens optical system and the distal end of the optical fiber are located between a distal end and a proximal end of the window in the directions parallel to the longitudinal axis.

2. The light irradiating device according to claim 1, wherein an inner peripheral end of the lens-side facing portion is located to an inner peripheral direction side of an outer peripheral end of the fiber-side facing portion, and an outer peripheral end of the lens-side facing portion is located to an outer peripheral direction side of an inner peripheral end of the fiber-side facing portion.

3. The light irradiating device according to claim 1, wherein the lens optical system includes a most-proximal lens which is a lens located on the most proximal direction side, and which has a proximal end to be the proximal end of the lens optical system, and the lens-side cylindrical portion includes a lens frame in which the lens-side facing portion is provided, and to which the most-proximal lens is fixed so that the lens-side facing portion and the proximal end of the most-proximal lens are located on the same reference plane perpendicular to the longitudinal axis.

4. The light irradiating device according to claim 3, wherein the fiber-side cylindrical portion includes a fiber distal end accommodating cylinder in which the fiber-side facing portion is provided, and which accommodates the distal end of the optical fiber so that the distal end of the optical fiber is located to the proximal direction side of the fiber-side facing portion.

5. The light irradiating device according to claim 4, wherein the lens-side facing portion is located at a proximal end of the lens frame, and the fiber-side facing portion is located at a distal end of the fiber distal end accommodating cylinder.

6. The light irradiating device according to claim 3, wherein the inner peripheral end of the fiber-side facing portion is located to the outer peripheral direction side of an outer peripheral side of the most-proximal lens.

7. The light irradiating device according to claim 1, further comprising an actuator section which is configured to drive the optical fiber so that the distal end of the optical fiber moves on a substantially planar surface perpendicular to the longitudinal axis, and which is configured to change, with time, a position in the subject where the light is collected by the lens optical system.

8. The light irradiating device according to claim 1, wherein the first dimension is 0.2 mm or less.

9. A scanning endoscopic device comprising:
the light irradiating device according to claim 1;
an actuator section which is configured to drive the optical fiber so that the distal end of the optical fiber moves on a substantially planar surface perpendicular to the longitudinal axis, and which is configured to change, with time, a position in the subject where the light is collected by the lens optical system;

a light guide which is extended along the longitudinal axis, and which is configured to receive, with time, light reflected from the collection position of the subject, the light guide being configured to guide the received light from the distal direction to the proximal direction; and a light detector which is configured to detect, with time, a kind and an intensity of light guided by the light guide.

10. The scanning endoscopic device according to claim 9, further comprising:
a drive current supplier which is configured to supply a drive current to the actuator section, and which is configured to drive the optical fiber;

a collection position detector which is configured to detect, with time, the collection position in the subject in accordance with the drive current supplied from the drive current supplier; and an image processing section which is configured to generate the image of the subject in accordance with the kind and the intensity of light detected by the light detector with time and the collection position detected by the collection position detector with time.

11. A manufacturing method of a light irradiating device of a scanning endoscopic device which is configured to scan a subject to generate an image of the subject, the manufacturing method comprising:

attaching an optical fiber to a fiber-side cylindrical portion of a cylindrical unit so that the movement of the optical fiber along a longitudinal axis is regulated, the optical fiber being extended along the longitudinal axis, and being configured to emit, from a distal end thereof, light guided from a proximal direction to a distal direction;

fixing a lens optical system to a lens-side cylindrical portion of the cylindrical unit, the lens optical system having a proximal end thereof located apart from the distal end of the optical fiber in directions parallel to the longitudinal axis in an in-focus condition, the lens optical system being configured to collect the light emitted from the optical fiber to the subject in the in-focus condition;

forming, in the fiber-side cylindrical portion, a fiber-side facing portion which faces in the distal direction in the in-focus condition;

forming a lens-side facing portion in the lens-side cylindrical portion, the lens-side facing portion facing in the proximal direction in the in-focus condition, the lens-side facing portion facing the fiber-side facing portion apart from the fiber-side facing portion by a second dimension smaller than a first dimension between the distal end of the optical fiber and the proximal end of the lens optical system in the directions parallel to the longitudinal axis in the in-focus condition;

forming a hole which forms a window in the in-focus condition along diametrical directions from an outer portion to an inner portion of the cylindrical unit, the hole being formed so that the proximal end of the lens optical system and the distal end of the optical fiber are located between a distal end and a proximal end of the window in the directions parallel to the longitudinal axis in the in-focus condition;

adjusting relative positions of the fiber-side cylindrical portion and the lens-side cylindrical portion in the directions parallel to the longitudinal axis to positions in the in-focus condition through the window formed in the cylindrical unit so that the lens optical system fixed to the lens-side cylindrical portion is located to the distal direction side of the optical fiber attached to the fiber-side cylindrical portion and so that the fiber-side cylindrical portion and the lens-side cylindrical portion are disposed coaxially with the longitudinal axis; and fixing the fiber-side cylindrical portion and the lens-side cylindrical portion at the adjusted relative positions.

12. The manufacturing method according to claim 11, further comprising forming an actuator section configured to drive the optical fiber so that the distal end of the optical fiber moves on a substantially planar surface perpendicular to the longitudinal axis, the actuator section being formed to use the movement of the distal end of the optical fiber in the in-focus condition to change, with time, a position in the subject where the light is collected by the lens optical system.

13. A manufacturing method of a scanning endoscope, the manufacturing method comprising:

forming a light irradiating device by the manufacturing method according to claim 12;

attaching a light guide to the light irradiating device, the light guide being extended along the longitudinal axis, the light guide being configured to receive, with time, light reflected from the collection position of the subject, the light guide being configured to guide the received light from the distal direction to the proximal direction; and attaching an envelope tube to the light irradiating device and the light guide so that the light irradiating device and the light guide are contained therein, the envelope tube forming a part of an outer surface.

14. The manufacturing method according to claim 11, wherein forming the lens-side facing portion includes forming the lens-side facing portion so that an inner peripheral end of the lens-side facing portion is located to an inner peripheral direction side of an outer peripheral end of the fiber-side facing portion and so that an outer peripheral end of the lens-side facing portion is located to an outer peripheral direction side of an inner peripheral end of the fiber-side facing portion in the in-focus condition.

15. The manufacturing method according to claim 11, wherein attaching the optical fiber to the fiber-side cylindrical portion includes attaching the optical fiber to the fiber-side cylindrical portion so that the distal end of the optical fiber is accommodated in a fiber distal end accommodating cylinder of the fiber-side cylindrical portion, fixing the lens optical system to the lens-side cylindrical portion includes fixing a most-proximal lens to a lens frame of the lens-side cylindrical portion, the most-proximal lens being a lens located on the most proximal direction side and having a proximal end to be the proximal end of the lens optical system, forming the fiber-side facing portion includes forming the fiber-side facing portion in the fiber distal end accommodating cylinder so that the distal end of the optical fiber is located to the proximal direction side of the fiber-side facing portion, and forming the lens-side facing portion includes forming the lens-side facing portion in the lens frame so that the lens-side facing portion and the proximal end of the most-proximal lens are located on the same reference plane perpendicular to the longitudinal axis in the in-focus condition.

16. The manufacturing method according to claim 15, wherein forming the fiber-side facing portion in the fiber distal end accommodating cylinder includes forming the fiber-side facing portion at a distal end of the fiber distal end accommodating cylinder, and forming the lens-side facing portion in the lens frame includes forming the lens-side facing portion at a proximal end of the lens frame.

17. The manufacturing method according to claim 15, wherein fixing the most-proximal lens to the lens frame includes fixing the most-proximal lens so that the inner peripheral end of the fiber-side facing portion is located to the outer peripheral direction side of an outer peripheral end of the most-proximal lens in the in-focus condition.

18. The manufacturing method according to claim 11, wherein adjusting the relative positions of the fiber-side cylindrical portion and the lens-side cylindrical portion includes adjusting the relative positions of the fiber-side cylindrical portion and the lens-side cylindrical portion in the directions parallel to the longitudinal axis to positions in the in-focus condition where the first dimension is 0.2 mm or less.

* * * * *